(12) United States Patent
Saguchi et al.

(10) Patent No.: US 9,549,546 B2
(45) Date of Patent: *Jan. 24, 2017

(54) SUSTAINED RELEASE PREPARATION COMPRISING INSECT PEST-TARGETING GEL COMPOSITION

(71) Applicant: SHIN-ETSU CHEMICAL CO., LTD., Tokyo (JP)

(72) Inventors: Ryuichi Saguchi, Joetsu (JP); Tatsuya Hojo, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/362,259

(22) PCT Filed: Dec. 6, 2012

(86) PCT No.: PCT/JP2012/081627
§ 371 (c)(1),
(2) Date: Jun. 2, 2014

(87) PCT Pub. No.: WO2013/084983
PCT Pub. Date: Jun. 13, 2013

(65) Prior Publication Data
US 2014/0328790 A1    Nov. 6, 2014

(30) Foreign Application Priority Data

Dec. 9, 2011    (JP) ................. 2011-270132

(51) Int. Cl.
| A01N 25/04 | (2006.01) |
| A01N 25/34 | (2006.01) |
| A01N 31/02 | (2006.01) |
| A01N 35/02 | (2006.01) |
| A01N 37/06 | (2006.01) |
| A01N 43/90 | (2006.01) |
| A01N 25/18 | (2006.01) |

(52) U.S. Cl.
CPC ........... *A01N 25/04* (2013.01); *A01N 25/18* (2013.01); *A01N 25/34* (2013.01); *A01N 31/02* (2013.01); *A01N 35/02* (2013.01); *A01N 37/06* (2013.01); *A01N 43/90* (2013.01)

(58) Field of Classification Search
CPC ........ A01N 25/04; A01N 31/04; A01N 37/02; A01N 37/44; A01P 19/00
See application file for complete search history.

(56) References Cited

U.S. PATENT DOCUMENTS

| 4,353,962 | A | 10/1982 | Himel et al. | |
| 4,817,868 | A | 4/1989 | Cook et al. | |
| 6,065,687 | A | 5/2000 | Suzuki et al. | |
| 6,242,509 | B1 | 6/2001 | Berger et al. | |
| 2001/0055604 | A1 | 12/2001 | Kalder et al. | |
| 2005/0208085 | A1* | 9/2005 | Yamato et al. | 424/401 |
| 2006/0093638 | A1 | 5/2006 | Hojo et al. | |
| 2007/0148202 | A1 | 6/2007 | Primo Yufera et al. | |

FOREIGN PATENT DOCUMENTS

| EP | 0160151 | A2 | 11/1985 |
| EP | 0572743 | A1 | 12/1993 |
| EP | 1142959 | | * 10/2001 |
| JP | 59-216802 | | 12/1984 |
| JP | 63-222104 | | 9/1988 |
| JP | 02-207002 | | 8/1990 |
| JP | 02-207003 | | 8/1990 |
| JP | 07-267809 | | 10/1995 |
| JP | 11-069936 | | 3/1999 |
| JP | 2001-515840 | | 9/2001 |
| JP | 2002-306584 | | 10/2002 |
| JP | 2004-275010 | A | 10/2004 |
| JP | 2006-124330 | A | 5/2006 |
| WO | WO 03/079778 | A1 | 10/2003 |
| WO | WO 2004/014438 | | 2/2004 |

OTHER PUBLICATIONS

Heuskin et al ("The Use of Semiochemical Slow-release Devices in Integrated Pest Management Strategies", Biotechnol. Agron. Soc. Environ, 2011, vol. 15(3), pp. 459-470).*
Patent Examination Report No. 1 corresponding to Australian Patent Application No. 2012261590 issued May 17, 2013.
Heuskin et al. "The use of semiochemical slow-release devices in integrated pest management strategies", *Biotechnol. Agron. Soc. Environ*. 15(3):459-470 (2011).
International Search Report corresponding to International Application No. PCT/JP2012/081627 mailed Jan. 29, 2013.
International Preliminary Report on Patentability corresponding to International Application No. PCT/JP2012/081627 mailed Jun. 10, 2014.
Material Data Safety Sheet for Bushman Ultra—Water Resistant Insect Repellent (2008) 6 pages.
Product Description of Bushman DryGel Insect Repellent http://web.archive.org/web/20100222095936/http://www.bushman-repellent.com/products.htm retrieved Apr. 14, 2015 (3 pages).
Extended European Search Report corresponding to European Application No. 12854702.3 issued Apr. 21, 2015.
Extended European Search Report corresponding to European Application No. 12856107.3 issued Apr. 21, 2015.
Extended European Search Report corresponding to European Application No. 12856554.6 issued Apr. 22, 2015.
Office Action corresponding to Japanese Application No. 2012-265265 issued Sep. 4, 2015.
Office Action corresponding to Japanese Application No. 2012-265266 issued Jul. 28, 2015.
Office Action corresponding to Japanese Application No. 2012-265267 issued Jul. 28, 2015.

* cited by examiner

*Primary Examiner* — Suzanne Ziska
(74) *Attorney, Agent, or Firm* — Myers Bigel, P.A.

(57) ABSTRACT

Provided is a sustained release preparation comprising an insect pest-targeting gel composition, the preparation being free from leakage or reaction of a volatile substance and being capable of releasing the volatile substance at a constant rate. More specifically, provided is a sustained release preparation including a polymer tube and an insect pest-targeting gel composition in the polymer tube, the composition including one or more volatile substances and an oil gelling agent, wherein the volatile substances are included in an amount of from 70.0 to 99.0% by weight by the insect pest-targeting composition and are released outside of the polymer tube through the polymer tube.

2 Claims, 5 Drawing Sheets

SUSTAINED RELEASE PREPARATION COMPRISING INSECT PEST-TARGETING GEL COMPOSITION

RELATED APPLICATIONS

This application is a 35 U.S.C. §371 national stage application of PCT Application No. PCT/JP2012/081627, filed on Dec. 6, 2012, which claims priority from Japanese Application No. 2011-270132, filed on Dec. 9, 2011, the contents of which are incorporated herein by reference in their entireties. The above-referenced PCT International Application was published as International Publication No. WO 2013/084983 A1 on Jun. 13, 2013.

TECHNICAL FIELD

This invention relates to a sustained release preparation comprising an insect pest-targeting gel composition.

BACKGROUND ART

Mating disruption, emergence forecasting, mass trapping, control of insect pests in a predetermined area and the like can be accomplished by the sustained release of a pheromone substance, an attractant, a repellent or the like. As a method of sustainably releasing a volatile substance which is effective for insect pest control, over a long period of time, a method of sustainably releasing a volatile substance in liquid form, a method of sustainably releasing a volatile substance in gel form and other methods are known. For example, Patent Document 1 discloses a method comprising the steps of enclosing a volatile substance in a polymer vessel and sustainably releasing it from the polymer surface through the polymer wall; Patent Document 2 discloses a method comprising the steps of forming a volatile substance into a fluid gel and sustainably releasing the gel through a polymer film; and Patent Document 3 discloses a method comprising the steps of entrapping a volatile substance in a polymer lattice and sustainably releasing it in a solid or gel form.

PRIOR ART DOCUMENTS

Patent Documents

[Patent Document 1] JP 07-313035A/1995
[Patent Document 2] JP 2002-306584A
[Patent Document 3] JP 64-055136A/1989

SUMMARY OF THE INVENTION

Problem to be Solved by the Invention

However, a preparation obtained by the method comprising the step of enclosing a volatile substance in liquid form in a polymer vessel as described in Patent Document 1 has a problem that holes or cracks are caused in the vessel as a result of rude treatment by users upon use and the volatile substance enclosed in the vessel leaks from it so that the release period is markedly decreased. The fluid gel described in Patent Document 2 also has a problem, in addition to the possibility of leakage, that a large amount of diluent has to be added to give fluidity so that the release rate of the volatile substance is decreased as the time elapses. Accordingly, there is a demand for the development of a sustained release preparation which can release a volatile substance at a constant rate without causing leakage of the volatile substance.

The polymer gel described in Patent Document 3 has no possibility of leakage of the volatile substance. However, since the gel is produced by polymerization in the presence of a volatile substance, the method cannot be applied to a volatile substance having an instable functional group which may react under polymerization conditions. Accordingly, there is a strong demand for the development of a sustained release preparation in gel form which can be produced without exposing the volatile substance to severe conditions such as polymerization conditions.

The present invention has been made with the foregoing in view. An object thereof is to provide a sustained release preparation comprising an insect pest-targeting gel composition, which preparation can sustainably release a volatile substance at a constant rate without causing leakage or reaction of the volatile substance.

Solution to the Problem

In order to achieve the above-mentioned object, the present inventors have studied a sustained release preparation comprising an insect pest-targeting gel composition, which preparation can sustainably and stably release a volatile substance effective for insect pest control at a given or faster rate over a long period of time. As a result, it has been unexpectedly found that the above-mentioned object is achieved by producing a sustained release preparation comprising a polymer tube and an insect pest-targeting gel composition in the polymer tube, the composition comprising one or more volatile substances and an oil gelling agent, wherein the volatile substances are comprised in an amount of from 70.0 to 99.0% by weight by the insect pest-targeting gel composition and is released outside of the polymer tube through the wall of the polymer tube. Thus, the invention has been completed.

Effect of the Invention

According to the invention, the sustained release preparation comprising an insect pest-targeting gel composition can reduce the possibility of leakage of a volatile substance and suppress a loss of the volatile substance due to the reaction at the time of gelling because the volatile substance is gelled under mild conditions. In addition, the sustained release preparation does not contain a diluent component such as a solvent so that the release at a given or faster rate can be maintained stably for a long period of time. Furthermore, the release rate can be regulated, depending on the material, thickness or the like of the polymer tube. Even a volatile substance having high volatility and therefore not suited for use in conventional sustained release preparations can be released stably when used in the sustained release preparation of the invention.

EMBODIMENTS FOR CARRYING OUT THE INVENTION

The sustained release preparation of the invention comprises a polymer tube and an insect pest-targeting gel composition in the polymer tube, the composition comprising one or more volatile substances and an oil gelling agent. As a material of the polymer tube, a material which can release a volatile substance from the polymer tube to the outside through the wall of the polymer tube is used. Examples of the volatile substance to be used in the invention include a pheromone substance, an attractant, a repellent and a mixture thereof.

Examples of the pheromone substance to be used in the invention include a linear aliphatic aldehyde having from 12 to 20 carbon atoms, a linear aliphatic acetate having from 12 to 20 carbon atoms which is saturated or has one or more double bonds, a linear aliphatic alcohol having from 7 to 20 carbon atoms, a spiroacetal having from 7 to 15 carbon atoms, a linear aliphatic ketone having from 10 to 25 carbon atoms, an aliphatic hydrocarbon having from 10 to 30 carbon atoms, and a carboxylic acid having from 10 to 20 carbon atoms. Of these examples, a linear aliphatic aldehyde having from 12 to 20 carbon atoms, a linear aliphatic acetate having from 12 to 20 carbon atoms which is saturated or has one or more double bonds, a linear aliphatic alcohol having from 7 to 20 carbon atoms and a spiroacetal having from 7 to 15 carbon atoms are particularly preferred. Specific examples include Z7Z11-hexadecadienyl acetate and Z7E11-hexadecadienyl acetate which are the sex pheromone substances of the pink bollworm (*Pectinophora gossypiella*); Z-8-dodecenyl acetate which is the sex pheromone substance of the oriental fruit moth (*Grapholita molesta*); E-5-decenyl acetate which is the sex pheromone substance of the peach twig borer (*Anarsia lineatella*); Z-9-dodecenyl acetate which is the sex pheromone substance of the grape berry moth (*Eupoecilia ambiguella*); E7Z9-dodecadienyl acetate which is the sex pheromone substance of the European grape vine moth (*Lobesia botrana*); E-11-tetradecenyl acetate which is the sex pheromone substance of the light brown apple moth (*Epiphyas postvittana*); E8E10-dodecadienol which is the sex pheromone substance of the codling moth (*Cydia pomonella*); Z-11-tetradecenyl acetate which is the sex pheromone substance of the leaf roller (Tortricidae); Z3-Z13-octadecadienyl acetate and E3Z13-octadecadienyl acetate which are the sex pheromone substances of the peach tree borer (*Synanthedon exitiosa*); Z11-hexadecenal which is the sex pheromone substance of the American bollworm (*Helicovema armigera*); Z9-hexadecenal which is the pheromone substance of the oriental tobacco bud worm (*Heliothis assulta*); E8E10-dodecadienyl acetate which is the sex pheromone substance of the soybean pod borer (*Leguminivora glycinivorella*); Z-11-hexadecenyl acetate and Z-11-hexadecenal which are the sex pheromone substances of the diamondback moth (*Plutella xylostella*); Z-11-hexadecenyl acetate, Z-11-hexdecenol and n-hexadecyl acetate which are the sex pheromone substances of the cabbage armyworm (*Mamestra brassicae*); Z9E12-tetradecadienyl acetate and Z-9-tetradecenol which are the sex pheromone substances of the beat armyworm (*Spodoptera exigua*); Z9E11-tetradecadienyl acetate and Z9E12-tetradecadienyl acetate which are the sex pheromone substances of the common cutworm (*Spodoptera litura*); Z-9-tetradecenyl acetate which is the sex pheromone substance of the fall armyworm (*Spodoptera frugiperda*); E-4-tridecenyl acetate which is the sex pheromone substance of the tomato pinworm (*Keiferia lycopersicella*); Z-11-hexadecenal and Z-13-octadecenal which are the sex pheromone substances of the rice stem borer (*Scirpophaga incertulas*); 5,9-dimethylpentadecane and 5,9-dimethylhexadecane which are the sex pheromone substance of the coffee leaf miner (*Leucoptera coffeella*); 14-methyl-1-octadecene which is the sex pheromone substance of the peach leaf miner (*Lyonetia clerkella* L.); Z-13-icosen-10-one which is the sex pheromone substance of peach fruit moth (*Caiposina sasakii*); 7,8-epoxy-2-methyloctadecane which is the sex pheromone substance of the gypsy moth (*Lymantria dispar dispar*); Z-13-hexadecen-1-nyl acetate which is the sex pheromone substance of the pine processionary moth (*Thaumetopoea pityocampa*); 2-butanol which is the sex pheromone substance of the white grub beetle (*Dasylepida ishigakiensis*); Z-7,15-hexadecadien-4-olide which is the sex pheromone substance of the yellowish elongate chafer (*Heptophylla picea*); n-dodecyl acetate which is the sex pheromone substance of the sugarcane wireworm (*Melanotus okinawensis*); E-9,11-dodecadienyl butyrate and E-9,11-dodecadienyl hexanate which are the sex pheromone substances of the sugarcane wireworm (*Melanotus sakishimensis*); (R)—Z-5-(oct-1-enyl)-oxacyclopentan-2-one which is the sex pheromone substance of the cupreous chafer (*Anomala cuprea*); hexyl hexanoate, E-2-hexenyl hexanoate and octyl butyrate which are the sex pheromone substances of the rice leaf bug (*Trigonotylus caelestialium*); hexyl butyrate, E-2-hexenyl butyrate and E-4-oxo-2-hexenal which are the sex pheromone substances of the sorghum plant bug (*Stenotus rubrovittatus*); (6R)—Z-3,9-dimethyl-6-isopropenyl-3,9-decadienyl propionate and (6R)—Z-3,9-dimethyl-6-isopropenyl-3,9-decadienol which are the sex pheromone substances of the white peach scale (*Pseudaulacaspis pentagona*); (S)-5-methyl-2-(1-propen-2-yl)-4-hexenyl 3-methyl-2-butenoate which is the sex pheromone substance of the vine mealybug (*Planococcus ficus*); Z-9-tricosene which is the sex pheromone substance of the housefly (*Musca domestica*); gentisyl quinone isovalerate which is the sex pheromone of the German cockroach (*Blattella germanica*); and 1,7-dioxaspiro[5.5]undecane which is the sex pheromone substance of the olive fruit fly (*Bactrocera oleae*).

Other examples of the pheromone substance to be used in the invention include a linear aliphatic aldehyde having from 12 to 20 carbon atoms, a linear aliphatic acetate having from 12 to 20 carbon atoms which is saturated or has one or more double bonds, a linear aliphatic alcohol having from 7 to 20 carbon atoms, a spiroacetal having from 7 to 15 carbon atoms, a linear aliphatic ketone having from 10 to 25 carbon atoms, an aliphatic hydrocarbon having from 10 to 30 carbon atoms and a carboxylic acid having from 10 to 20 carbon atoms, other than those exemplified above.

Specific examples of the linear aliphatic aldehyde having from 10 to 20 carbon atoms include Z-5-decenal, 10-undecenal, n-dodecanal, Z-9-dodecenal, E5Z10-dodecadienal, E8E10-dodecadienal, n-tetradecanal, Z7-tetradecenal, Z9-tetradecenal, Z11-tetradecenal, Z9E11-tetradecadienal, Z9Z11-tetradecadienal, Z9E12-tetradecadienal, Z9E11,13-tetradecatrienol, Z10-pentadecenal, E9Z11-pentadecadienal, n-hexadecanal, Z7-hexadecenal, E6Z11-hexadecadienal, E4Z6-hexadecadienal, E4E6Z11-hexadecatrienal, E10E12E14-hexadecatrienal, n-octadecanal, Z9-octadecenal, E14-octadecenal, E2Z13-octadecadienal, Z3Z13-octadecadienal, Z9Z12-octadecadienal, and Z9Z12Z15-octadecatrienal.

Specific examples of the linear aliphatic acetate having from 12 to 20 carbon atoms which is saturated or has a double bond include decyl acetate, Z3-decenyl acetate, Z4-decenyl acetate, undecyl acetate, Z7-undecenyl acetate, Z8-undecenyl acetate, E9-undecenyl acetate, dodecyl acetate, E7-dodecenyl acetate, Z7-dodecenyl acetate, E8-dodecenyl acetate, E9-dodecenyl acetate, 11-dodecenyl acetate, 10-methyldodecenyl acetate, tridecyl acetate, Z4-tridecenyl acetate, E6-tridecenyl acetate, E8-tridecenyl acetate, Z8-tridecenyl acetate, tetradecyl acetate, Z7-tetradecenyl acetate, E8-tetradecenyl acetate, Z8-tetradecenyl acetate, E9-tetradecenyl acetate, Z9-tetradecenyl acetate, E10-tetradecenyl acetate, Z10-tetradecenyl acetate, E12-tetradecenyl acetate, Z12-tetradecenyl acetate, 12-methyltetradecenyl acetate, pentadecyl acetate, Z8-pentadecenyl acetate, E9-pentadecenyl acetate, hexadecyl acetate, Z3-hexadecenyl acetate, Z5-hexadecenyl acetate, E6-hexadecenyl acetate, Z7-hexadecenyl acetate, Z9-hexadecenyl acetate, Z10-hexadecenyl acetate, Z12-hexadecenyl acetate, heptadecyl acetate, Z11-heptadecenyl acetate, octadecyl acetate, E2-octadecenyl acetate, Z11-octadecenyl acetate, and E13-octadecenyl acetate.

Specific examples of the linear aliphatic acetate having from 12 to 20 carbon atoms and having two or more double bonds include a conjugated diene-based and/or 1,4-pentadiene-based acetate such as Z3E5-decadienyl acetate, Z3E5-dodecadienyl acetate, E3Z5-dodecadienyl acetate, E4Z10-dodecadienyl acetate, Z5E7-dodecadienyl acetate, E5Z7-dodecadienyl acetate, Z8Z10-dodecadienyl acetate, 9,11-dodecadienyl acetate, E4Z7-tridecadienyl acetate, 11-methyl-Z9,12-tridecadienyl acetate, E3E5-tetradecadienyl acetate, E8E10-tetradecadienyl acetate, Z10Z12-tetradecadienyl acetate, Z10E12-tetradecadienyl acetate, E10Z12-tetradecadienyl acetate, E10E12-tetradecadienyl acetate, E11,13-tetradecadienyl acetate, Z8Z10-pentadecadienyl acetate, Z8E10-pentadecadienyl acetate, Z8Z10-hexadecadienyl acetate, Z10E12-hexadecadienyl acetate, Z11Z13-hexadecadienyl acetate, Z11E13-hexadecadienyl acetate, E11Z13-hexadecadienyl acetate, and Z11E14-hexadecadienyl acetate.

Specific examples of the linear aliphatic alcohol having from 7 to 20 carbon atoms include a saturated linear aliphatic alcohol and a linear aliphatic alcohol having one or more double bonds such as n-heptanol, Z4-heptenol, Z6-nonenol, Z6,8-nonadienol, E6,8-nonadienol, n-decanol, Z5-decenol, E5-decenol, n-undecanol, undecenol, 11-chloro-E8E10-undecadienol, n-dodecanol, Z5-dodecenol, Z7-dodecenol, E7-dodecenol, Z8-dodecenol, E8-dodecenol, Z9-dodecenol, E9-dodecenol, E10-dodecenol, 11-dodecenol, Z5E7-dodecadienol, E5Z7-dodecadienol, E5E7-dodecadienol, Z7Z9-dodecadienol, Z7E9-dodecadienol, E7Z9-dodecadienol, 8,9-difluoro-E8E10-dodecadienol, 10,11-difloro-E8E10-dodecadienol, 8,9,10,11-tetrafluoro-E8E10-dodecadienol, Z9,11-dodecadienol, E9,E11-dodecadienol, n-tridecanol, n-tetradecanol, Z5-tetradecenol, E5-tetradecenol, Z7-tetradecenol, Z8-tetradecenol, Z11-tetradecenol, E11-tetradecenol, Z9Z11-tetradecadienol, Z9E11-tetradecadienol, Z9Z12-tetradecadienol, Z9E12-tetradecadienol, Z10Z12-tetradecadienol, E10E12-tetradecadienol, n-pentadecanol, 6,10,14-trimethyl-2-pentadecanol, n-hexadecanol, Z9-hexadecenol, Z11-hexadecenol, E11-hexadecenol, Z7Z11-hexadecadienol, Z7E11-hexadecadienol, E10Z12-hexadecadienol, E10E12-hexadecadienol, Z11Z13-hexadecadienol, Z11E13-hexadecadienol, E11Z13-hexadecadienol, E1Z13-hexadecadienol, E4Z6Z10-hexadecatrienol, E4E6Z10-hexadecatrienol, n-octadecanol, Z13-octadecenol, E2Z13-octadecadienol, Z3Z13-octadecadienol, E3Z13-octadecadienol and n-eicosanol.

Specific examples of the spiroacetal having from 7 to 15 carbon atoms include 1,6-dioxaspiro[4.5]decane, 2-ethyl-1,6-dioxaspiro[4.4]nonane, 3-hydroxy-1,7-dioxaspiro[5.5]undecane, 4-hydroxy-1,7-dioxaspiro[5.5]undecane, 7-methyl-1,6-dioxaspiro[4.5]decane, 2-methyl-1,6-dioxaspiro[4.5]decane, 2,7-dimethyl-1,6-dioxaspiro[4.4]nonane, 2,4,8-trimethyl-1,7-dioxaspiro[5.5]undecane, 2-methyl-1,7-dioxaspiro[5.5]undecane, 1,7-dioxaspiro[5.6]dodecane, 2,8-dimethyl-1,7-dioxaspiro[5.5]undecane, 2,2,8-trimethyl-1,7-dioxaspiro[5.5]undecane, 2-ethyl-1,7-dioxaspiro[5.5]undecane, 2-methyl-1,7-dioxaspiro[5.6]dodecane, 2-ethyl-7-methyl-1,6-dioxaspiro[5.6]decane, 7-ethyl-2-methyl-1,6-dioxaspiro[5.6]decane, 2,7-diethyl-1,6-dioxaspiro[4.4]nonane, 2,7-dimethyl-1,6-dioxaspiro[4.6]undecane, 2-methyl-7-propyl-1,6-dioxaspiro[4.4]nonane, 3-hydroxy-2,8-dimethyl-1,7-dioxaspiro[5.5]undecane, 2-propyl-1,7-dioxaspiro[5.5]undecane, 2-ethyl-8-methyl-1,7-dioxaspiro[5.5]undecane, 8-ethyl-2-methyl-1,7-dioxaspiro[5.5]undecane, 2,7-diethyl-1,6-dioxaspiro[4.5]decane, 2,7-dipropyl-1,6-dioxaspiro[4.4]nonane, 7-butyl-2-methyl-1,6-dioxaspiro[4.5]decane, 8-methyl-2-propyl-1,7-dioxaspiro[5.5]undecane, and 2-propyl-8-methyl-1,7-dioxaspiro[5.5]undecane.

Specific examples of the linear aliphatic ketone having from 10 to 25 carbon atoms include heptadecan-2-one, Z12-nonadecen-9-one, Z6Z9-nonadecadien-3-one, Z13-icosen-10-one, Z6-heneicosen-11-one, Z6-heneicosen-9-one, Z6E8-heneicosadien-11-one, Z6E9-heneicosadien-11-one, Z6Z9-heneicosadien-11-one, and Z7-tricosen-11-one.

Specific examples of the aliphatic hydrocarbon having from 10 to 30 carbon atoms include 1E11-pentadecadiene, 1Z11-pentadecadiene, 5,9-dimethylpentadecane, 2-methylhexadecane, 3,13-dimethylhexadecane, 5,9-dimethylhexadecane, n-heptadecane, 2-methylheptadecane, 2,5-dimethylheptadecane, 5-methylheptadecane, 5,11-dimethylheptadecane, 7-methylheptadecane, 7,11-dimethylheptadecane, Z3Z6Z9-heptadecatriene, Z6Z9-heptadecadiene, Z7-octadecene, 10,14-dimethyl-1-octadecene, 5,9-dimethyloctadecane, 2-methyloctadecane, 14-methyloctadecane, Z3Z6Z9-octadecatriene, n-nonadecane, 2-methylnonadecane, 9-methylnonadecane, Z3Z6Z9Z11-nonadecatetraene, 1E3Z6Z9-nonadecatetraene, Z3Z6Z9-nonadecatriene, Z6Z9-nonadecadiene, Z9-nonadecene, n-eicosane, Z9-eicosene, Z3Z6-eicosadiene, Z3Z6Z9-eicosatriene, 1Z3Z6Z9-eicosatetraene, 1Z3Z6Z9-heneicosatetraene, n-heneicosane, Z3Z6-heneicosadiene, Z6Z9-heneicosadiene, Z6Z9,20-heneicosatriene, Z3Z6Z9-heneicosatriene, Z6-13-methylheneicosene, Z9-heneicosene, n-docosaene, Z3Z6Z9-docosatriene, Z3Z6Z9-docosadiene, n-tricosane, Z7-tricosene, Z3Z6Z9-tricosatriene, Z6Z9-tricosadiene, n-tetracosane, n-pentacosane, Z3Z6Z9-pentacosatriene, n-hexacosane, n-heptacosane, n-octacosane, and n-nonacosane.

Specific examples of the carboxylic acid having from 10 to 20 carbon atoms are not particularly limited insofar they contain a carboxyl group. Examples include carboxylic acids having, in the carbon skeleton thereof, two or more methyl groups, one or more double bond or the like, such as 3,5-dimethyldodecanoeic acid, Z-5-undecenoic acid, E-5-undecenoic acid, and (E,Z)-3,5-tetradecadienoic acid.

Specific examples of the attractant include an aliphatic carboxylic acid such as formic acid, acetic acid, propionic acid, n-butyric acid, isobutyric acid, n-valeric acid, isovaleric acid, caproic acid, isocaproic acid, E2-butenoic acid, 2-hydroxypropionic acid and malonic acid; an aliphatic aldehyde such as acetaldehyde, propanal, pentanal and E2-hexanal; an aliphatic ketone such as 2-butanone, pentane-2,4-dione and cyclohexanone; an aliphatic carboxylate ester such as ethyl lactate, ethyl acetate, isoamyl acetate, Z3-hexenyl acetate, decyl acetate, hexyl 2-methylbutyrate, butyl hexanoate, ethyl octanoate, ethyl nonanoate, ethyl decanoate, ethyl undecanoate, ethyl dodecanoate, ethyl myristate, ethyl palmitate, ethyl E2Z4-decadienoate, tert-butyl 2-methyl-4-cyclohexenecarboxylate and tert-butyl 4 (or 5)-chloro-2-methyl-cyclohexanecarboxylate; an aliphatic alcohol such as ethanol, isobutyl alcohol, isopentyl alcohol, 2-ethylhexanol, Z3-hexenol, 1-octen-3-ol, nonanol, decanol, cyclohexanol, acetoin and propane 1,2-diol; an aliphatic ether such as diethyl ether and acetal; an aliphatic hydrocarbon such as α,β-ionone, undecane, tridecane, hexadecane, heptadecane and Z9-tricosene; an aromatic compound such as methyl phenylacetate, ethyl phenylacetate, propyl phenylacetate, phenetyl phenylacetate, Z3-hexenyl benzoate, eugenol, methyl isoeugenol, methyl eugenol, veratric acid, 2-allyloxy-3-ethoxybenzaldehyde, 4-(p-acetoxyphenyl)-2-butanone, 4-(p-hydroxyphenyl)-2-butanone (Raspberry ketone), anisylacetone, methyl anthranilate, ethyl anthranilate, benzyl salicylate, methyl salicylate, phenethyl alcohol, phenethyl propionate, phenethyl butyrate, anethole, vanillin, ethyl vanillin, isovanillin, heliotropin, piperonal acetone and phthiocol; a heterocyclic compound such as maltol, ethyl maltol, 2,5-dimethylpyrazine, γ-(4-pentenyl)-γ-butyrolactone, δ-nonyllactone and frontalin; a sulfur-containing compound such as dimethyl disulfide, dimethyl trisulfide, dipropyl disulfide, methyl isothiocyanate and 3-butenyl isothiocyanate; a nitrogen-containing compound such as trimethylamine, hexylamine, 1,4-diaminobutane, allylnitrile and methyl 2-amino-3-methylvalerate; and a terpene compound such as geraniol, farnesol, linalool, linalool oxide, citronellol, cineol, geranyl acetate, citronellyl acetate, citral, carvone, d-limonene, β-pinene, farnesene and 4,8-dimethyl-1,E3,7-nonatriene.

Other specific examples of the attractant include an essential oil such as angelica oil, citronella oil and mustard oil; and an extract from a plant such as aloe and eucalyptus.

Specific examples of the repellent include an aliphatic carboxylic acid such as Z9Z12-octadienoic acid and 3,7,11-trimethyl-6,10-dodecadinoic acid; an aliphatic aldehyde such as E2-hexenal, Z2E6-3,7-dimethyloctadienal, 3,7-dimethyl-6-octenal and E2Z6-nonadienal; an aliphatic ketone such as 2-heptanone, 2-dodecanone, 2-tridecanone, 3-methyl-2-cyclohexenone, E3E5-octadien-2-one and E3Z7-decadien-2-one; an aliphatic carboxylate ester such as butyl acetate, octyl acetate, methyl myristate, methyl palmitate and methyl 6-n-pentylcyclonexene-1-carboxylate; an aliphatic alcohol such as octanol, 1-octen-3-ol, 2-ethyl-1,3-hexanediol, menthol and n-hexyltriethylene glycol monoether; an aliphatic hydrocarbon such as tridecane; an aromatic compound such as cinnamic alcohol, cinnamic aldehyde, methyleugenol, phenyl acetaldehyde, benzaldehyde, anethole, diethyltoluamide, N,N-diethyl-3-methylbenzamide (DEET), dimethyl phthalate, dioctyl phthalate and naphthalene; a heterocyclic compound such as γ-nonyllactone, butyl 3,4-dihydro-2,2-dimethyl-4-oxo-2H-pyran-6-carboxylate, furfural and 4-octanoyl morpholine; a sulfur-containing compound such as propyl isothiocyanate; a nitrogen-containing compound such as methyl piperidine, 2,6-dimethylpiperidine and 2-ethylpiperidine; and a terpene compound such as geraniol, cineol, linalool, terpineol, citral, citronellal, neryl formate, a-pinene, carvone, d-limonene and camphor.

Additional examples may include an essential oil such as rose geranium oil, sandalwood oil, pepper oil (peppermint oil) and lemongrass oil; and an extract from a plant such as cinnamon, camphor, clover, thyme, geranium, bergamot, laurel, pine, *Gaultheria adenothrix*, pennyroyal, eucalyptus and neem tree.

The oil gelling agent to be used in the invention has, in the molecule thereof, at least one polar functional group capable of forming an intermolecular hydrogen bond such as a carboxyl group, a hydroxyl group, an ester group or an amide group, so that the intermolecular hydrogen bonds are present through the polar functional group. When the oil gelling agent is dissolved uniformly in the volatile substance by heating (preferably at from 60 to 150° C.), the intermolecular hydrogen bonds of the oil gelling agent are cut temporarily, but are formed again by cooling (including cooling by being left standing). Since a large amount of the volatile substance exists around the molecules of the oil gelling agent, the oil gelling agent forms the intermolecular hydrogen bonds again while incorporating therein the volatile substance. Only weak interaction such as Van der Waals force works between the volatile substance and the molecules of the oil gelling agent so that the volatility of the volatile substance even after gelling is almost the same as that before gelling.

Specific examples of the oil gelling agent include an amino acid derivative, a long-chain fatty acid, a polyvalent metal salt of a long-chain fatty acid, a sugar derivative and wax. Of these examples, an amino acid derivative and a long-chain fatty acid are particularly preferred.

Specifically preferred examples of the amino acid derivative include an amino-acylated and carboxyl-esterified or carboxyl-amidated derivative of an amino acid having from 2 to 15 carbon atoms, such as di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, N-lauroyl-L-glutamic acid dibutylamide, and N-ethylhexanoyl-L-glutamic acid dibutylamide. Of these examples, N-lauroyl-L-glutamic acid dibutylamide and N-ethylhexanoyl-L-glutamic acid dibutylamide are particularly preferred.

Specific examples of the long-chain fatty acid include a saturated or unsaturated fatty acid having from 8 to 24 carbon atoms, and an analog of a long-chain fatty acid such as 12-hydroxystearic acid. Specific examples of the saturated fatty acid include octanoic acid, 2-ethylhexanoic acid, decanoic acid, lauric acid, myristic acid, stearic acid, palmitic acid, arachidic acid and behenic acid. Specific examples of the unsaturated fatty acid include palmitoleic acid, oleic acid, vaccenic acid, linoleic acid, linolenic acid, arachidonic acid, icosadienoic acid and erucic acid.

Specific examples of the metal salt of a long-chain fatty acid include a metal salt of the long-chain fatty acid described above and a metal salt of a saturated fatty acid, for example, having a carbon chain of 18 carbon atoms such as aluminum stearate, magnesium stearate, manganese stearate, iron stearate, cobalt stearate, calcium stearate and lead stearate.

Specific examples of the saccharide derivative include a dextrin fatty acid ester such as dextrin laurate, dextrin myristate, dextrin palmitate, dextrin margarate, dextrin stearate, dextrin arachidate, dextrin lignocerate, dextrin cerotate, dextrin 2-ethylhexanoate palmitate and dextrin palmitate stearate; a sucrose fatty acid ester such as sucrose palmitate, sucrose stearate and sucrose acetate/stearate; a fructooligosaccharide fatty acid ester such as fructooligosaccharide stearate and fructooligosaccharide 2-etylhexanoate; and a benzylidene derivative of sorbitol such as monobenzylidene sorbitol and dibenzylidene sorbitol.

Specific examples of the wax include haze wax (Japan wax derived from *Rhus succedanea* seeds; main component: triglyceride of palmitic acid), urushi wax (Japan wax derived from *Rhus verniciflua*; main component: glyceride palmitate), carnauba wax (myricyl cerotate and myricyl alcohol), sugarcane wax (myricyl palmitate), palm wax (myricyl palmitate), beeswax (cerotic acid and myricyl palmitate), whale wax (cetyl palmitate), wool wax (ceryl alcohol and/or myristic acid) and paraffin wax (linear hydrocarbon).

A critical gelling concentration at which a volatile substance gels differs, depending on the structure of a polar functional group, the strength of hydrogen bonds and an asymmetric structure of the oil gelling agent. The strength of hydrogen bonds of the oil gelling agent is sometimes weakened by the coordination of the functional group (polar group) and a non-polar group of the volatile substance. The critical gelling concentration differs, depending on the chemical structure of the volatile substance and the kind of the gelling agent. In consideration of the release performance and cost, the gel composition is charged in the polymer tube desirably at a concentration near the critical gelling concentration. More specifically, the insect pest-targeting gel composition comprises therein from 70.0 to 99.0% by weight, preferably from 85.0 to 99.0% by weight, still more preferably from 90.0 to 99.0% by weight of the volatile substance. When the amount of the volatile substance in the insect pest-targeting gel composition is less than 70.0% by weight, the active ingredient of the volatile substance is enclosed in the gel so that the volatile substance cannot be released stably, thereby making it impossible to achieve long-term and constant sustained-release. In addition, it may increase the cost. When the volatile substance in the insect pest-targeting gel composition exceeds 99.0% by weight, the insect pest-targeting gel composition having fluidity only can be obtained.

For example, when Z11-tetradecenyl acetate, which is the pheromone substance of a leaf roller, is used as the volatile substance and stearic acid is used as the oil gelling agent, the resulting insect pest-targeting gel composition comprises preferably from 90 to 99% by weight of Z11-tetradecenyl acetate. When E8E10-dodecadienol, which is the pheromone substance of the codling moth, is used as the volatile substance and stearic acid is used as the oil gelling agent, the resulting insect pest-targeting gel composition comprises preferably from 70 to 80% by weight of E8E10-dodecadienol. When E8E10-dodecadienol is used as the volatile substance and N-lauroyl-L-glutamic acid dibutylamide is used as the oil gelling agent, the resulting insect pest-targeting gel composition comprises preferably from 90 to 97% by weight of E8E10-dodecadienol.

In the conventional gel composition, it is the common practice to dilute the gel composition with a solvent or the like to form a fluid gel in order to avoid a problem that the surface of the insect pest-targeting gel composition is dried to enclose the active ingredient of the volatile substance in the gel. However, when the gel contains a solvent or the like, it is difficult to obtain a stable release rate because due to the volatility of the solvent, the concentration of the volatile substance in the gel composition changes along with the sustained release. Moreover, this dilution causes problems such as necessity of measures against liquid leakage and unnecessary increase in volume. With the foregoing in view, as described above, the sustained release preparation in the invention comprises, in a polymer tube thereof, an insect pest-targeting gel composition comprising a volatile substance and an oil gelling agent, wherein the volatile substance is comprised in an amount of from 70.0 to 99.0% by weight by the insect pest-targeting gel composition.

The insect pest-targeting gel composition of the invention does not require measures against liquid leakage because it is a non-fluid gel comprising, in addition to the volatile substance, substantially only the oil gelling agent and an optional additive which will be described later. Furthermore, it does not cause the unnecessary volume increase because it does not comprise a solvent or the like. Moreover, the volatile substance in the insect pest-targeting gel composition is released to the surroundings and the gelling agent which has contributed to the gelling of the sustainably released volatile substance remains on the gel surface in powder form so that the concentration of the volatile substance in the insect pest-targeting gel composition becomes substantially constant throughout the release period, making it possible to achieve a stable release rate.

Thus, the insect pest-targeting gel composition of the invention is in non-fluid form, can be stored for a long period of time, and fluidization of the insect pest-targeting gel composition does not occur insofar as it is stored at normal temperature.

The insect pest-targeting gel composition may comprise an additive. The examples of the additive include an antioxidant such as a synthetic antioxidant, e.g., BHT (butylhydroxytoluene), BHA (butylhydroxyanisole), ethyl protocatechuate, isoamyl gallate and propyl gallate, and a natural antioxidant, e.g., NDGA (nordihydroguaiaretic acid) and guaiac gum; and a ultraviolet absorber such as a para-aminobenzoic acid-based one, e.g., octyl para-dimethylaminobenzoate, a benzophenone derivative such as oxybenzone (2-hydroxy-4-methoxy-benzophenone) and 2-hydroxy-4-octoxybenzophenone, a methoxycinnamic acid derivative and a salicylic acid derivative. The content of each additive in the insect pest-targeting gel composition is preferably from 0.01 to 5% by weight and the total content of them is preferably from 0.02 to 10% by weight.

The insect pest-targeting gel composition can be obtained by heating the volatile substance, the oil gelling agent and an optional additive preferably at about 60 to 150° C. for dissolution, and then cooling the resulting solution. The cooling is preferably cooling by being left standing.

According to the invention, a polymer tube (polymer tube) is used as a vessel into which the insect pest-targeting gel composition is introduced. The polymer tube is not particularly limited insofar as it uses a material of permitting penetration, transmission and/or diffusion of one or more volatile substances therethrough and allowing the one or more volatile substances be released (for example, evaporated) from the outer surface of the tube. Specific examples of the material include a thermoplastic polymer such as low-density polyethylene, high-density polyethylene, polypropylene, ethylene-propylene copolymers, ethylene vinyl acetate copolymers, ethylene acrylate ester-based copolymers, polyvinyl acetate, polyvinyl chloride-based resins, polymethyl methacrylate, polyvinyl alcohol, polyvinylidene chloride, polybutylene, methyl methacrylate-styrene copolymers, methylpentene resins, ionomers, polyacetal, cellulose acetate, cellulose acetate butyrate, polyvinylidene fluoride, and silicon resins. Examples of a biodegradable polymer include condensation polymers between at least one dicarboxylic acid selected from the group consisting of oxalic acid, malonic acid, succinic acid, glutaric acid, adipic acid, sebacic acid, fumaric acid and maleic acid, and at least one polyol selected from the group consisting of ethylene glycol, propylene glycol, butanediol, pentanediol, hexanediol, octanediol and decanediol; condensation polymers of at least one monomer selected from group consisting of lactic acid, hydroxyvaleric acid, hydroxycaproic acid and hydroxycapric acid; and an aliphatic polyester-based thermoplastic polymer such as polycaprolactone obtained by ring-opening polymerization of $\epsilon$-caprolactone. To these polymer materials, a lubricant, a plasticizer, a stabilizer, a pigment or a filler may be added to improve their processability.

The polymer tube may be sealed at either one end or both ends thereof, or may be open with an opening portion at either one end or both ends thereof. It is preferable to seal the tube at both ends in order to prevent a reaction such as oxidation or hydrolysis which will otherwise occur due to direct contact between the volatile substance and an outside environment.

The release rate of the volatile substance can be regulated by the material or thickness of the polymer tube. It can also be regulated by the presence or absence of the opening portion, but a ratio of the opening portion relative to the total area of the thin tube including the side surface of the tube from which the substance is released is small so that regulation of the release rate by the presence or absence of the opening portion is limited.

With regard to the shape, the polymer tube has preferably an inner diameter of from 0.5 to 15 mm, a thickness of from 0.2 to 1.5 mm, and a length of from 10 to 5,000 mm. The polymer tube includes an ampoule.

The amount of the insect pest-targeting composition to be introduced into each polymer tube is preferably from 10 mg/tube to 6 g/tube, though it varies, depending on the kind of the volatile substance, a period of application or the like.

The tubes each filled with the insect pest-targeting gel composition are installed in a field preferably at from 20 tubes/ha to 100,000 tubes/ha, though it may vary, depending on a target insect pest.

The method for producing the sustained release preparation of the invention include a method of molding to form a polymer tube material while filling the resulting polymer tube material with a gel composition solution comprising the volatile substance and the oil gelling agent; and a method of molding to form a polymer tube material and then filling the resulting polymer tube material with a gel composition solution.

The method of molding to form a polymer tube material while filling the resulting polymer tube material with a gel composition solution includes a method of extruding to continuously form an infinitely-long polymer tube material which has been filled with a prepared gel composition. More specifically, a molten polymer is extruded into a tubular form through a die to form a polymer tube material and at the same time, the polymer tube material is continuously filled with a prepared gel composition solution comprising a volatile substance and an oil gelling agent through a hole provided in the mandrel of the die. After an elongated polymer tube material is thus obtained, it is taken up on a reel. The resulting elongated polymer tube material is cut into pieces of an appropriate length, or welded by a hot press at intervals of an appropriate length and then cut into pieces. Consequently, a sustained release preparation comprising a polymer tube having both ends opened, or a sustained release preparation comprising a polymer tube having at least one end sealed can be obtained.

On the other hand, the method of molding to form a polymer tube material and then filling the resulting tube material with a gel composition solution includes a method comprising the steps of extruding to continuously form an elongated polymer tube material, dividing the material into portions, each having a necessary length, and then filling them with the prepared gel composition solution by pressure application or suction. After the gel composition solution becomes solidified, the polymer tube material is cut into a desired length, or welded and cut into a desired length. Consequently, a sustained release preparation comprising a polymer tube having both ends opened or having at least one end sealed can be obtained.

Figure 1:
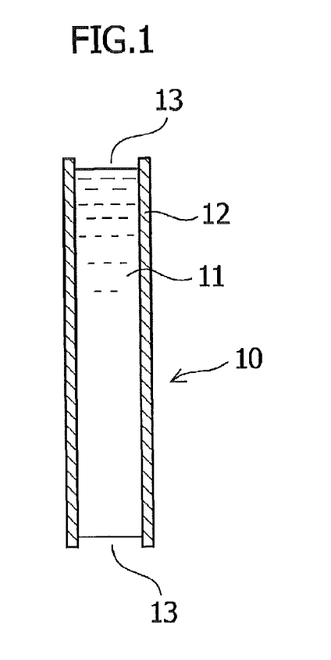
FIG. 1 shows one example of a sustained release preparation comprising a polymer tube having both ends opened.

FIG. 1 exhibits an example of a sustained release preparation comprising a polymer tube having both ends opened. The sustained release preparation 10 shown in FIG. 1 comprises a polymer tube 12 having an opening at each end 13 thereof, and an insect pest-targeting gel composition 11 in the polymer tube 12. The volatile substance penetrates and diffuses through the wall of the vessel, and is released from the outer surface of the sustained release preparation 10 to the outside space.

Figure 2:
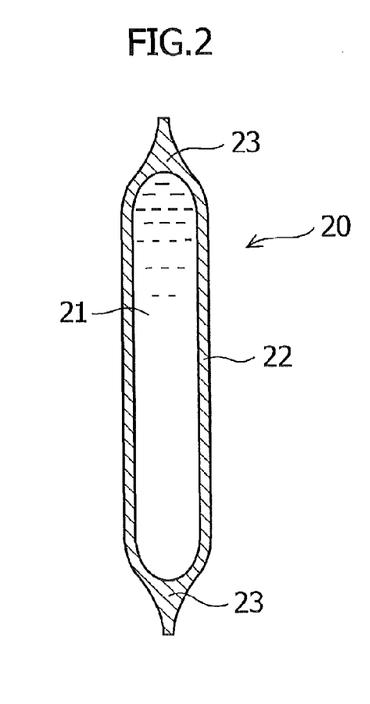
FIG. 2 shows one example of a sustained release preparation comprising a polymer tube having both ends sealed.

FIG. 2 exhibits an example of a sustained release preparation comprising a polymer tube having both ends sealed. The sustained release preparation 20 shown in FIG. 2 comprises a polymer tube 22 having both ends 23 sealed, and an insect pest-targeting gel composition 21 in the polymer tube 22. The volatile substance penetrates and diffuses through the wall of the vessel in the same manner and is released from the outer surface of the sustained release preparation 20 to the outside space.

EXAMPLES

The invention will be explained based on Examples. However, it should not be construed that the invention is limited to Examples.

Example 1

Simultaneously with extrusion of a polymer tube material made of an ethylene/vinyl acetate copolymer (having a vinyl acetate content of 4% by weight) and having an inner diameter of 1.2 mm and a film thickness of 0.50 mm, the tube material was filled with a uniform solution prepared by adding dextrin myristate to E8E10-dodecadienol at the weight ratio of 10:90 and heating the resulting mixture to a temperature of 80° C. Thus, simultaneous extrusion and filling were carried out. It was confirmed as a result of observing the inside of the polymer tube material that the solution gelled in non-fluid form at room temperature. The resulting polymer tube material was cut into 200-mm long pieces to obtain sustained-release preparations, each comprising a tube having both ends opened.

The sustained release preparations thus obtained were allowed to stand under the conditions of 25° C. and a wind speed of 0.7 m/sec to release the volatile substance therefrom. A decrease in the weight was measured with the elapsed time so that a release rate of E8E10-dodecadienol was determined. The results are shown in FIG. 3.

Figure 3:
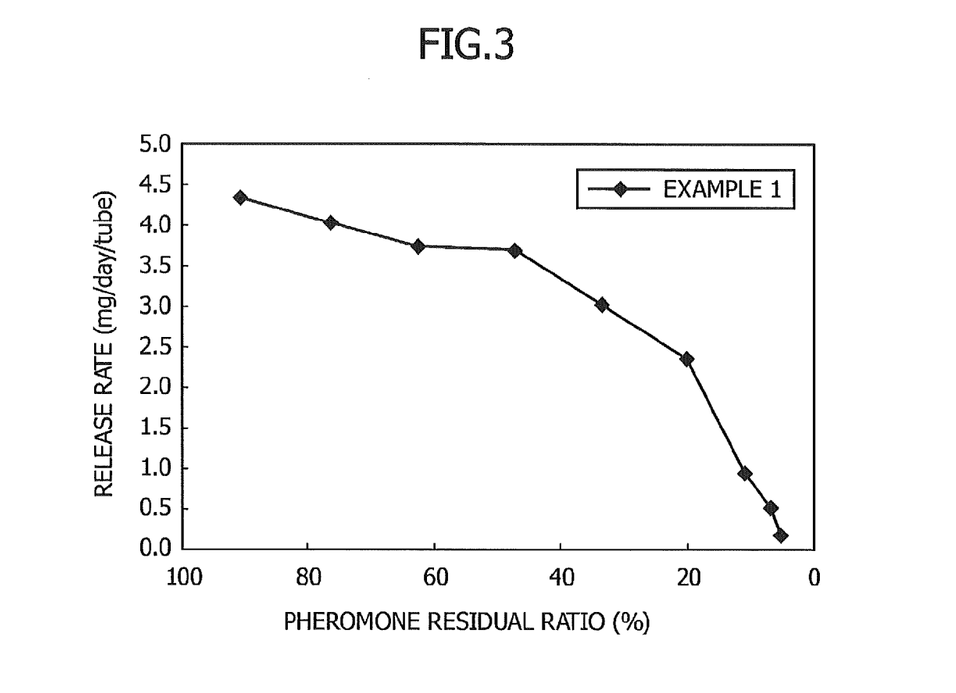
FIG. 3 is a graph showing the relationship between a pheromone residual ratio and a release rate in Example 1.

As shown in FIG. 3, the resulting sustained release preparations released E8E10-dodecadienol for long a long period of time and E8E10-dodecadienol did not leak out by way of fluidization during the release period.

Example 2

Simultaneously with extrusion of a polymer tube material made of a polybutylene adipate/polybutylene succinate copolymer and having an inner diameter of 1.0 mm and a film thickness of 0.40 mm, the material was filled with a uniform solution prepared by adding N-lauroyl-L-glutamic acid dibutylamide to Z8-dodecenyl acetate at the weight ratio of 2.5:97.5 and heating the resulting mixture to a temperature of 95° C. Thus, simultaneous extrusion and filling were carried out. It was confirmed as a result of observing the inside of the polymer tube material that the solution gelled in non-fluid form at room temperature. The polymer tube material was cut into 200-mm pieces and at the same time, preparations (in Example 2A), each comprising a tube having one end welded and sealed, and preparations (in Example 2B), each comprising a tube having both ends welded and sealed, were produced.

The sustained release preparations thus obtained were allowed to stand under the conditions of 30° C. and a wind speed of 0.7 m/sec to release the volatile substance from the sustained release preparations. A decrease in the weight was measured with the elapsed time so that a release rate of Z8-dodecenyl acetate was determined. The results are shown in FIG. 4.

Figure 4:
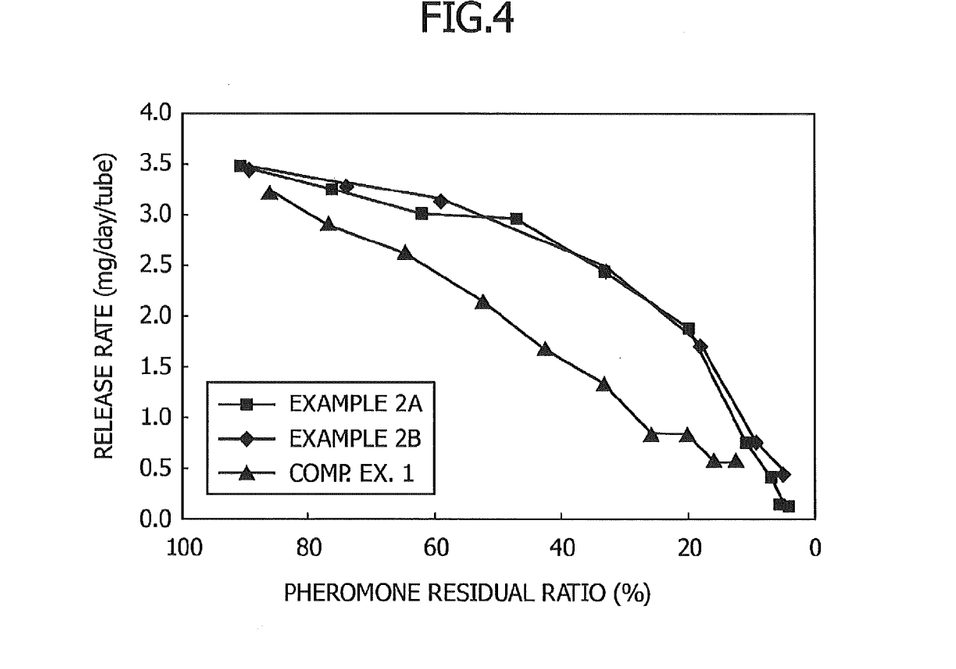
FIG. 4 is a graph showing the relationship between a pheromone residual ratio and a release rate in Example 2 and Comparative Example 1.

As shown in FIG. 4, the resulting sustained release preparations released Z8-dodecenyl acetate for a long period of time and Z8-dodecenyl acetate did not leak out by way of fluidization during the release period.

Example 3

Simultaneously with extrusion of a polymer tube material made of a polybutylene adipate/polybutylene succinate copolymer and having an inner diameter of 1.0 mm and a film thickness of 0.40 mm, the material was filled with a uniform solution prepared by adding N-ethylhexanoyl-L-glutamic acid dibutylamide to Z11-hexadecenal at the weight ratio of 3:97 and heating the resulting mixture to a temperature of 95° C. Thus, simultaneous extrusion and filling were carried out. It was confirmed as a result of observing the inside of the polymer tube material that the solution gelled in non-fluid at room temperature. The polymer tube material was cut into 200-mm pieces to obtain sustained-release preparations, each comprising a tube having both ends opened.

The sustained release preparations thus obtained were allowed to stand under the conditions of 30° C. and a wind speed of 0.7 m/sec to release the volatile substance therefrom. A decrease in the weight was measured with the elapsed time so that a release rate of Z11-hexadecenal was determined. The results are shown in FIG. 5.

Figure 5:
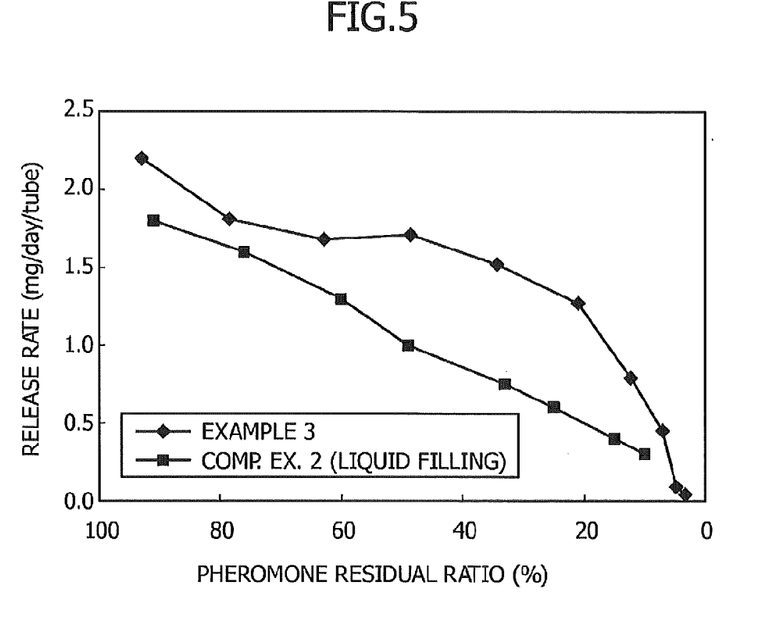
FIG. 5 is a graph showing the relationship between a pheromone residual ratio and a release rate in Example 3 and Comparative Example 2.

As shown in FIG. 5, the resulting sustained release preparations released Z11-hexadecenal for a long period of time and Z11-hexadecenal did not leak out by way of fluidization during the release period.

Example 4

A polymer tube material made of a polybutylene adipate/polybutylene succinate copolymer having an inner diameter of 1.0 mm and a film thickness of 0.40 mm was produced by extrusion. The 2-butanol, the sex pheromone substance of the white grub beetle, was subject to addition of N-ethylhexanoyl-L-glutamic acid dibutylamide at the weight ratio of 93:7, followed by heating under stirring. The resulting solution became uniform at 65° C. After further heating to 70° C., the resulting solution was introduced into the polymer tube material by suction. The tube material thus obtained was then allowed to stand at room temperature for 2 hours. It was confirmed as a result of observing the inside of the polymer tube material that the solution gelled in non-fluid form at room temperature. The polymer tube material was cut into 200-mm pieces to obtain sustained-release preparations, each comprising a tube having both ends opened.

The sustained release preparations were allowed to stand under the conditions of 25° C. and a wind speed of 0.7 msec to release the volatile substance therefrom. A decrease in the weight was measured with the elapsed time so that a release rate of 2-butanol was determined. The results are shown in FIG. 6.

Figure 6:
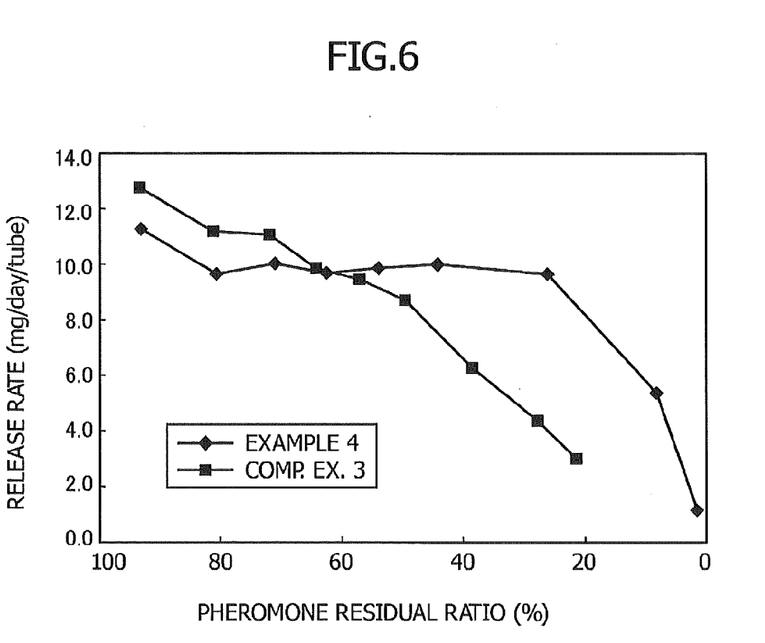
FIG. 6 is a graph showing the relationship between a pheromone residual ratio and a release rate in Example 4 and Comparative Example 3.

As shown in FIG. 6, the resulting sustained release preparations continued to release 2-butanol for 30 days or more and 2-butanol did not leak out by way of fluidization during the release period.

Example 5

A polymer tube material made of high-density polyethylene and having an inner diameter of 1.4 mm and a film thickness of 0.60 mm was produced by extrusion. The Z11-tetradecenyl acetate was subjected to addition of 12-hydroxystearic acid at the weight ratio of 94:6, followed by heating under stirring. Then the resulting solution became uniform at 60° C. After further heating to 80° C., the resulting solution was introduced into the polymer tube material by suction. The tube material thus obtained was then allowed to stand at room temperature for 2 hours. It was confirmed that the polymer tube material was filled with Z11-tetracedecyl acetate in non-fluid gel form. The polymer tube material thus obtained was cut into 200-mm pieces to obtain sustained-release preparations, each comprising a tube having both ends opened.

The sustained release preparations thus obtained were allowed to stand under the conditions of 30° C. and a wind speed of 0.7 msec to release the volatile substance therefrom. A decrease in the weight was measured with the elapsed time so that a release rate of Z11-tetradecenyl acetate was determined. The results are shown in FIG. 7.

Figure 7:
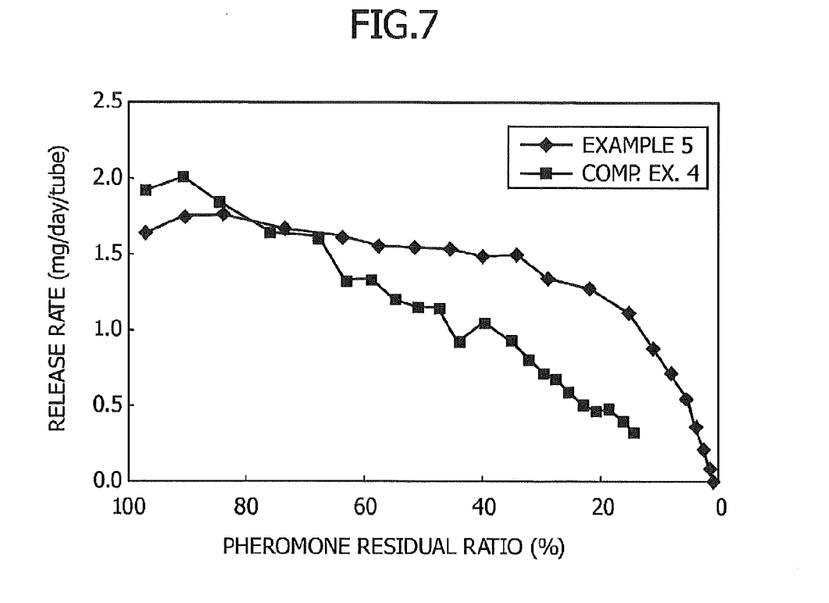
FIG. 7 is a graph showing the relationship between a pheromone residual ratio and a release rate in Example 5 and Comparative Example 4.

As shown in FIG. 7, the sustained release preparations thus obtained released Z11-tetradecenyl acetate for a long period of time and Z11-tetradecenyl acetate did not leak out by way of fluidization during the release period.

Example 6

A polymer tube material made of a polybutylene adipate/polybutylene succinate copolymer and having an inner diameter of 1.0 mm and a film thickness of 0.40 mm was produced by extrusion.

The E8E10-dodecadienol was subjected to addition of stearic acid at the weight ratio of 80:20, followed by heating under stirring. The resulting solution became uniform at 80° C. After further heating to 90° C., the resulting solution was introduced into the polymer tube material by suction. The tube material thus obtained was then allowed to stand at room temperature for 2 hours. It was confirmed that the polymer tube material was filled with E8E10-dodecadienol which had gelled in non-fluid form. The polymer tube material was cut into 200-mm pieces to obtain sustained release preparations, each comprising a tube having both ends opened.

The sustained release preparations were allowed to stand under the conditions of 25° C. and a wind speed of 0.7 msec to release the volatile substance therefrom. A decrease in the weight was measured with the elapsed time so that a release rate of E8E10-dodecadienol was determined. The results are shown in FIG. 8.

Figure 8:
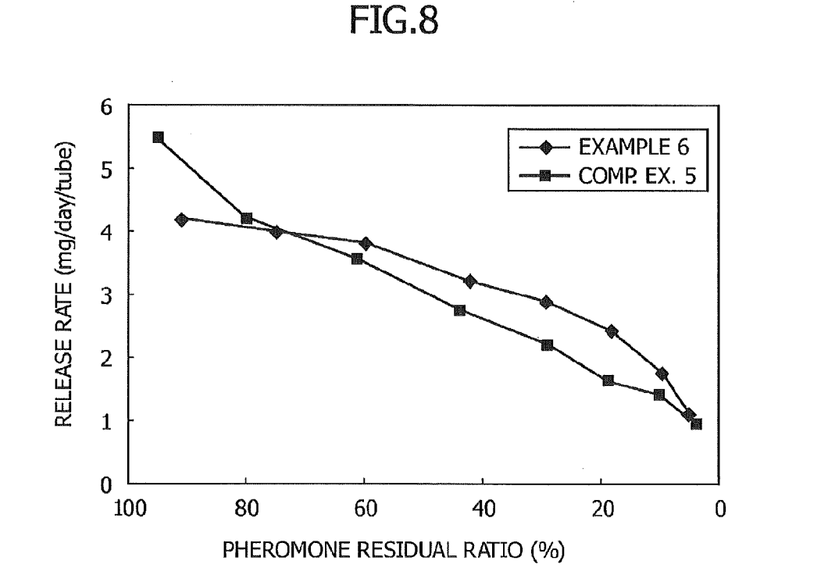
FIG. 8 is a graph showing the relationship between a pheromone residual ratio and a release rate in Example 6 and Comparative Example 5.

As shown in FIG. 8, the resulting sustained release preparations released E8E10-dodecadienol for a long period of time and E8E10-dodecadienol did not leak out by way of fluidization during the release period.

Example 7

A polymer tube material made of a polybutylene adipate/polybutylene succinate copolymer and having an inner diameter of 1.0 mm and a film thickness of 0.40 mm was produced by extrusion.

The Z9-hexadecenal was subjected to addition of stearic acid at the weight ratio of 94.5:5.5, followed by heating under stirring. The resulting solution became uniform at 80° C. After further heating to 90° C., the resulting solution was introduced into the polymer tube material by suction. The tube material thus obtained was then allowed to stand at room temperature for 2 hours. It was confirmed that the polymer tube material was filled with Z9-hexadecenal which had gelled in non-fluid form. The resulting polymer tube material was cut into 200-mm pieces to obtain sustained-release preparations, each comprising a tube having both ends opened.

The sustained release preparations were allowed to stand under the conditions of 30° C. and a wind speed of 0.7 m/sec to release the volatile substance therefrom. A decrease in the weight was measured with the elapsed time so that a release rate of Z9-hexadecenal was determined. The results are shown in FIG. 9.

Figure 9:
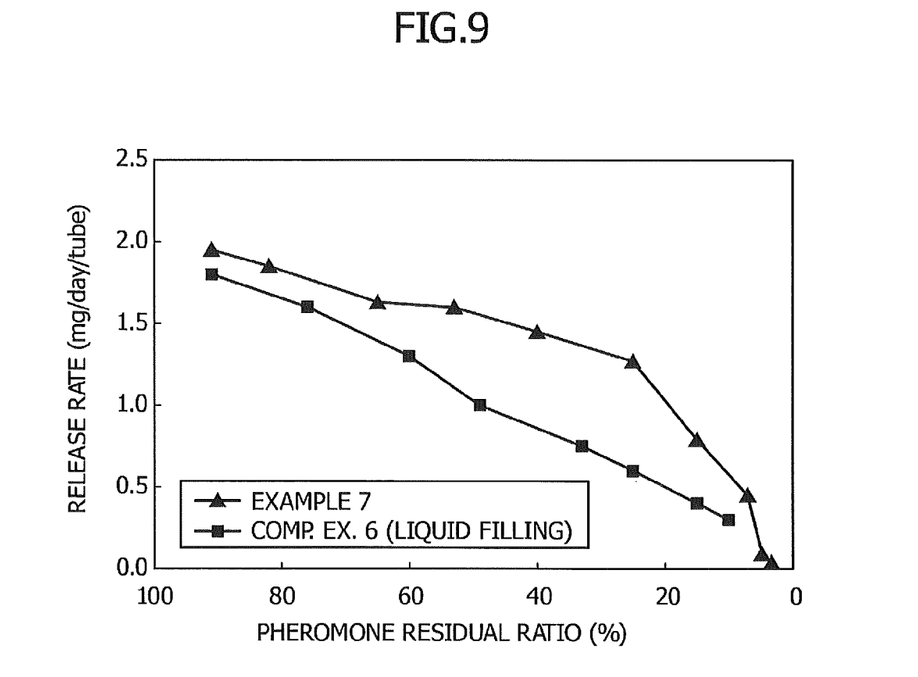
FIG. 9 is a graph showing the relationship between a pheromone residual ratio and a release rate in Example 7 and Comparative Example 6.

As shown in FIG. 9, the resulting sustained release preparations released Z9-hexadecenal for a long period of time and Z9-hexadecenal did not leak out by way of fluidization during the release period.

Comparative Example 1

Simultaneously with extrusion of a polymer tube material made of a polybutylene adipate/polybutylene succinate copolymer and having an inner diameter of 1.0 mm and a film thickness of 0.40 mm, the polymer tube material was filled with Z8-dodecenyl acetate (liquid filling).

The resulting polymer tube material was welded and cut at intervals of 200 mm to obtain sustained release preparations, each comprising a tube having both ends sealed.

The sustained release preparations thus obtained were allowed to stand under the conditions of 30° C. and a wind speed of 0.7 msec to release the volatile substance therefrom. A decrease in the weight was measured with the elapsed time so that a release rate of Z8-dodecenyl acetate was determined. The results are shown in FIG. 4.

As shown in FIG. 4, the release rate of Z8-dodecenyl acetate from the resulting sustained release preparations gradually decreased with the elapsed time and uniform release over a long period of time was not achieved.

Comparative Example 2

Simultaneously with extrusion of a polymer tube material made of a polybutylene adipate/polybutylene succinate copolymer and having an inner diameter of 1.0 mm and a film thickness of 0.40 mm, the tube material was filled with Z11-hexadecenal (liquid filling).

The resulting polymer tube material was ultrasonically sealed and cut at intervals of 200 mm to obtain sustained release preparations, each comprising a tube having both ends sealed.

The sustained release preparations thus obtained were allowed to stand under the conditions of 30° C. and a wind speed of 0.7 msec to release the volatile substance therefrom. A decrease in the weight was measured with the elapsed time so that a release rate of Z11-hexadecenal was determined. The results are shown in FIG. 5.

As shown in FIG. 5, the release rate of Z11-hexadecenal from the resulting sustained release preparations gradually decreased with the elapsed time and uniform release over a long period of time was not achieved.

Comparative Example 3

A polymer tube material made of a polybutylene adipate/polybutylene succinate copolymer and having an inner diameter of 1.0 mm and a film thickness of 0.40 mm was produced by extrusion. The polymer tube material thus obtained was filled with 2-butanol, the sex pheromone substance of the white grub beetle, by suction (liquid filling). The resulting polymer tube material was ultrasonically sealed and cut at intervals of 200 mm to obtain sustained release preparations, each comprising a tube having both ends sealed.

The sustained release preparations thus obtained were allowed to stand under the conditions of 30° C. and a wind speed of 0.7 msec to release the volatile substance therefrom. A decrease in the weight was measured with the elapsed time so that a release rate of 2-butanol was determined. The results are shown in FIG. 6.

As shown in FIG. 6, the release rate of 2-butanol from the resulting sustained release preparations gradually decreased with the elapsed time and uniform release over a long period of time was not achieved.

Comparative Example 4

A polymer tube material made of high-density polyethylene and having an inner diameter of 1.4 mm and a film thickness of 0.60 mm was produced by extrusion. The polymer tube material thus obtained was filled with Z11-tetradecenyl acetate by suction (liquid filling). The resulting polymer tube material was ultrasonically sealed and cut at intervals of 200 mm to obtain sustained release preparations comprising a tube having both ends sealed.

The sustained release preparations thus obtained were allowed to stand under the conditions of 30° C. and a wind speed of 0.7 msec to release the volatile substance therefrom. A decrease in the weight was measured with the elapsed time so that a release rate of Z11-tetradecenyl acetate was determined. The results are shown in FIG. 7.

As shown in FIG. 7, the release rate of Z11-tetradecenyl acetate from the resulting sustained release preparations gradually decreased with the elapsed time and uniform release over a long period of time was not achieved.

Comparative Example 5

A polymer tube material made of a polybutylene adipate/polybutylene succinate copolymer and having an inner diameter of 1.0 mm and a film thickness of 0.40 mm was produced by extrusion.

The E8E10-dodecadienol was subjected to addition of stearic acid, followed by heating under stirring. The resulting solution containing 35% by weight of stearic acid became uniform at 80° C. After the resulting solution was heated further to 90° C., the polymer tube material was filled with it by suction and allowed to stand at room temperature for 2 hours. It was confirmed that the polymer tube material was filled with E8E10-dodecadienol which had gelled in non-fluid form. The resulting polymer tube material was cut into 200-mm pieces to obtain sustained release preparations, each comprising a tube having both ends opened.

The sustained release preparations thus obtained were allowed to stand under the conditions of 25° C. and a wind speed of 0.7 msec to release the volatile substance therefrom. A decrease in the weight was measured with the elapsed time so that a release rate of E8E10-dodecadienol was determined. The results are shown in FIG. 8.

As shown in FIG. 8, the release rate of E8E10-dodecadienol from the resulting sustained release preparations gradually decreased with the elapsed time and uniform release over a long period of time was not achieved.

Comparative Example 6

A polymer tube material made of a polybutylene adipate/polybutylene succinate copolymer and having an inner diameter of 1.0 mm and a film thickness of 0.40 mm was produced by extrusion. The polymer tube material thus obtained was filled with Z9-hexadecenal by suction (liquid filling). The resulting polymer tube material was ultrasonically sealed and cut at intervals of 200 mm to obtain sustained release preparations, each comprising a tube having both ends sealed.

The sustained release preparations thus obtained were allowed to stand under the conditions of 30° C. and a wind speed of 0.7 m/sec to emit the volatile substance therefrom. A decrease in the weight was measured with the elapsed time so that a release rate of Z9-hexadecenal was determined. The results are shown in FIG. 9.

As shown in FIG. 9, the release rate of Z9-hexadecenal gradually decreased with the elapsed time and uniform release over a long period of time was not achieved.

EXPLANATION OF SYMBOLS

10, 20: sustained release preparation
11, 21: insect pest-targeting gel composition
13, 23 end

The invention claimed is:
1. A sustained release preparation comprising:
a polymer tube and,
an insect pest-targeting gel composition in the polymer tube, the composition comprising one or more volatile substances and an oil gelling agent selected from the group consisting of a long-chain fatty acid, a polyvalent metal salt of the long chain fatty acid, a saccharide derivative and wax, and wherein the sustained release preparation does not contain a solvent, wherein said one or more volatile substances are comprised in an amount of from 70.0 to 99.0% by weight by the insect pest-targeting gel composition and are released outside of the polymer tube through the polymer tube, and wherein the long-chain fatty acid is selected from the group consisting of 2-ethylhexanoic acid, decanoic acid, lauric acid, myristic acid, stearic acid, palmitic acid, arachidic acid, behenic acid, palmitoleic acid, oleic acid, vaccenic acid, linoleic acid, linolenic acid, arachidonic acid, icosadienoic acid and erucic acid.

2. The sustained, release preparation according to claim 1, wherein said one or more volatile substances are selected from the group consisting of a pheromone substance, an attractant and a repellent.

* * * * *

UNITED STATES PATENT AND TRADEMARK OFFICE
CERTIFICATE OF CORRECTION

| | | |
|---|---|---|
| PATENT NO. | : 9,549,546 B2 | Page 1 of 1 |
| APPLICATION NO. | : 14/362259 | |
| DATED | : January 24, 2017 | |
| INVENTOR(S) | : Saguchi et al. | |

It is certified that error appears in the above-identified patent and that said Letters Patent is hereby corrected as shown below:

In the Specification

Column 14, Lines 17 and 46: Please correct "0.7 msec" to read -- 0.7 m/sec --

Column 15, Lines 7 and 55: Please correct "0.7 msec" to read -- 0.7 m/sec --

Column 16, Lines 10, 32 and 53: Please correct "0.7 msec" to read -- 0.7 m/sec --

Column 17, Line 15: Please correct "0.7 msec" to read -- 0.7 m/sec --

Signed and Sealed this
Fifth Day of September, 2017

Joseph Matal
*Performing the Functions and Duties of the*
*Under Secretary of Commerce for Intellectual Property and*
*Director of the United States Patent and Trademark Office*